(12) United States Patent  
Ghoshal et al.

(10) Patent No.: US 7,420,043 B2  
(45) Date of Patent: *Sep. 2, 2008

(54) REAGENTS FOR DETECTING EFAVIRENZ

(75) Inventors: Mitali Ghoshal, Noblesville, IN (US); Gerald Sigler, Carmel, IN (US); Anlong Ouyang, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 731 days.

This patent is subject to a terminal disclaimer.

(21) Appl. No.: 10/732,767

(22) Filed: Dec. 10, 2003

(65) Prior Publication Data

US 2005/0131216 A1 Jun. 16, 2005

(51) Int. Cl.
*C07K 1/13* (2006.01)
*C07K 1/10* (2006.01)
*G01N 33/532* (2006.01)
*C07D 265/14* (2006.01)

(52) U.S. Cl. ............... 530/403; 530/402; 530/405; 530/406; 436/544; 544/105

(58) Field of Classification Search ............... 530/402, 530/403, 405, 406; 544/105; 436/544
See application file for complete search history.

(56) References Cited

U.S. PATENT DOCUMENTS 5,633,405 A     5/1997   Thompson et al. .......... 564/321
5,874,430 A *   2/1999   Christ et al. ............... 514/229.8
2004/0214251 A1* 10/2004 Sigler et al. ................ 435/7.92

FOREIGN PATENT DOCUMENTS

EP   1470825 A1     10/2004
WO   WO03/006506 A2  1/2003

OTHER PUBLICATIONS

Rizzo et al. Prediction of activity for nonnucleoside inhibitors with HIV-1 Reverse transcriptase based on monte carlo simulations. J. Med. Chem. 2002, vol. 45, pp. 2970-2987.*

Patel et al. Synthesis and evaluation of analogs of efavinz (Sustiva) as HIV-1 reverse transcriptase inhibitors. Bioorg. Med. Chem. Lett. 1999, pp. 2805-2810.*

Mutlib et al. "Identification and Characterization of Efavirenz Metabolites by Liquid Chromatography/Mass Spectrometry and High Field NMR: Species Differences in the Metabolism of Efavirenz". Drug Metabolism and Disposition, vol. 27, No. 11, pp. 1319-1333, 1999.

Marzolini et al., "Efavirenz plasma levels can predict treatment failure and central nervous system side effects in HIV-1-infected patents". AIDS 2001, 15: 71-75.

(Continued)

*Primary Examiner*—Long V. Le
*Assistant Examiner*—Shafiqul Haq
(74) *Attorney, Agent, or Firm*—Marilyn L. Amick; Roche Diagnostics Operations, Inc.

(57) ABSTRACT

The invention provides derivatives of efavirenz and methods of making derivatives of efavirenz. The derivatives include immunogenic compounds for producing antibodies to efavirenz and labeled efavirenz tracers. These compounds are useful in immunoassay methods for determining efavirenz.

4 Claims, 8 Drawing Sheets

OTHER PUBLICATIONS

Singh et al., "Cesium Fluoride Catalyzed Trifluoromethylation of Esters, Aldehydes, and Ketones with (Trifluoromethyl) Trimethylsilane", J. Org Chem 1999, 64, 2873-2876.

Radesca, et al., "Synthesis of HIV-1 Reverse Transcriptase Inhibitor DMP 266", Synthetic Communications, 27(24), 4373-4384 (1997).

Zhuyin Li et al., "New Synthesis and Characterization of (+) Lysergic Acid Diethylamide (LSD) Derivatives and the Development of a Microparticle-Based Immunoassay for the Detection of LDS and Its Metabolites", Bioconjugate Chem. 1997, 8, 896-905.

Prakash, G.K., Yudin AK, "Perfluoroalkylation with Organosilicon Reagents", Chem Rev 1997, 97, 757-786.

Patel, et al., "Synthesis and Evaluation of Analogs of Efavirenz (Sustiva™) as HIV-1 Reverse Transcriptase Inhibitors", Bioorganic & Medicinal Chemistry Letters 9 (1999), 2805-2810.

Akeb, F. et al., "Quantification of plasma and intracellular levels of the HIV protease inhibitor ritonavir by competitive ELISA," Journal of Immunological Methods 263 (2002) 1-9.

Rezk, N. et al., "Simple and rapid quantification of the non-nucleoside reverse transcriptase inhibitors nevirapine, delavirdine, and efavirenz in human blood plasma using high-performance liquid chromatography with ultraviolet absorbance detection," Journal of Chromatography B, 774 (2002) 79-88.

* cited by examiner

REAGENTS FOR DETECTING EFAVIRENZ

FIELD OF THE INVENTION

The invention relates to immunogens comprising efavirenz and to efavirenz derivatives for use in an immunoassay for the detection of efavirenz.

BACKGROUND OF THE INVENTION

Human immunodeficiency virus type-1 (HIV-1) is a retrovirus that leads to the development of acquired immune deficiency syndrome (AIDS). The infectivity rate of HIV in the United States has been estimated at about 40,000 new infections per year. Current treatments for HIV infection are designed to interfere with the ability of the virus to replicate by inhibiting either HIV protease or HIV reverse transcriptase (RT).

Efavirenz (SUSTIVA, Bristol-Meyers Squibb) is one of the FDA-approved drugs used in the treatment of patients infected with HIV. Efavirenz has been shown to lower the amount of HIV in the blood (the "viral load"). When taken with other anti-HIV medicines, efavirenz has been shown to reduce patients' viral load and to increase their CD4 cell count.

Clinical research has demonstrated that HIV can develop resistance to drugs used in HIV therapy, including efavirenz. Such drug resistance is thought to be a primary reason for therapy failure. The development of drug resistance in HIV may be a result of the virus rapid replication rate. Despite its potency, efavirenz has a low genetic barrier. A high level of phenotypic resistance can be induced by a single mutation, frequently at lysine 103 (K103N) in the RT gene. The emergence of efavirenz-resistant HIV mutants could be a result of repeated exposure to ineffective or sub-therapeutic drug levels.

Therapeutic failures are observed more frequently in patients having low serum concentrations of efavirenz. For example, Marzolini et al., AIDS 15 (London), 71-75, 2001, reported virological failure in 50% of patients (85 total patients) that had low plasma levels of efavirenz, e.g., <1000 μg/L. In patients with plasma levels of efavirenz that ranged from 1000-4000 μg/L, or more than 4000 μg/L, they observed virological failure in 18-22% of those patients. Moreover, 20-40% of patients receiving efavirenz reported central nervous system (CNS) side effects that include dizziness, hallucinations, nightmares, and insomnia. While these symptoms are usually mild to moderate in severity and are reported to subside progressively over a few weeks after the initiation of efavirenz therapy, it has been reported that about 4% of patients discontinue therapy because of the severity or persistence of these side effects. CNS toxicity was approximately three times more frequent in patients with high efavirenz levels, e.g., >4000 μg/L, compared with the patients having levels in the 1000-4000 μg/L range. This implies that treatment failure and CNS side effects are associated with low and high efavirenz plasma levels, respectively. The variability of efavirenz levels in individuals strongly supports that the dose adjustment should be based on therapeutic drug monitoring (TDM) in order to optimize beneficial therapeutic effects while minimizing CNS side effects.

As pharmacological differences among patients introduce wide heterogeneity in the response to antiviral therapy, monitoring of drug levels could be useful in the management of HIV infection as well as the disorders and diseases associated with HIV infection. Formal therapeutic drug monitoring of antiviral drugs useful in HIV therapy is known using high-performance liquid chromatographic (HPLC) methods (Marzolini et al., ibid.).

While HPLC methods can be used to determine efavirenz levels in plasma, such methods are impractical for commercial use due to, for example, long sample preparation time, long assay time, high cost, and labor-intensive procedures. Thus, a simple and fast analytical method for measurement of plasma levels of efavirenz is needed for effective TDM. Immunoassay techniques are well suited for such analytical applications.

Standard medical practice for treatment of HIV infections is to co-administer three HIV drugs, at least two of which come from different classes, for example, 2 nucleoside reverse transcriptase inhibitors (NRTI's) and a non-nucleoside reverse transcriptase inhibitor (NNRTI). Thus, for an immunoassay technique for measuring efavirenz, it is essential that an antibody be highly specific for efavirenz.

SUMMARY OF THE INVENTION

The present invention provides a compound having the structure wherein L is NH or O; $R_1$ is a saturated or unsaturated, substituted or unsubstituted, straight or branched chain of 0-10 carbon or hetero atoms; X is a linker group consisting of 0-2 substituted or unsubstituted aromatic rings or aliphatic linking groups containing 0-10 carbon or hetero atoms; and Y is an activated ester, maleimido group, thiol, or NH-Z where Z is a carrier or a label.

In another aspect, the invention provides an antibody produced in response to a compound having the structure wherein L is NH or O; $R_1$ is a saturated or unsaturated, substituted or unsubstituted, straight or branched chain of 0-10 carbon or hetero atoms; X is a linker group consisting of 0-2 substituted or unsubstituted aromatic rings or aliphatic linking groups containing 0-10 carbon or hetero atoms; and Y is NH-Z where Z is a carrier such as a poly(amino acid).

In another aspect, the invention provides monoclonal antibodies with high specificity for efavirenz over other commonly co-administered HIV drugs. These drugs include other non-nucleoside reverse transcriptase inhibitors (NNRTI's) such as nevirapine and delaviradine as well and nucleoside reverse transcriptase inhibitors (NRTI's) such as 3'-azido-3'-deoxythymidine and 2',3'-didehydro-3'-deoxythymidine, and protease inhibitors (PI's) such as nelfinavir, saquinavir, indinavir, ritonavir, amprenavir, lopinavir, and atazanavir.

Another aspect of the present invention provides a compound having the structure wherein L is NH or O; $R_1$ is a saturated or unsaturated, substituted or unsubstituted, straight or branched chain of 0-10 carbon or hetero atoms; X is a linker group consisting of 0-2 substituted or unsubstituted aromatic rings or aliphatic linking groups containing 0-10 carbon or hetero atoms; and Y is NH-Z where Z is a label such as an enzyme, fluorogenic compound, chemiluminescent material, electrochemical mediator, particle, reporter group, enzyme inhibitor, and nucleic acid.

Yet another aspect of the invention is the 6-hydroxy analog of efavirenz (9, chiral and racemic):

DETAILED DESCRIPTION OF THE INVENTION

"Efavirenz" refers to the compound that is the active ingredient in SUSTIVA (Bristol-Meyers Squibb), an FDA-approved drug used in the treatment of patients infected with HIV, the virus that can lead to development of AIDS. Efavirenz can be represented by the chemical structure:

The term "efavirenz" can be taken to encompass compounds that have the same substantial structure, including both chiral and racemic mixtures of the above structure, metabolites, and analogues thereof.

"Haptens" are partial or incomplete antigens. They are protein-free substances, mostly low molecular weight substances, which are not capable of stimulating antibody formation, but which do react with antibodies. The latter are formed by coupling a hapten to a high molecular weight carrier and then injecting this coupled product, i.e., immunogen, into a human or animal subject. Efavirenz is a hapten.

The term "derivative" refers to a chemical compound or molecule made from a parent compound or molecule by one or more chemical reactions.

An "activated hapten" refers to a hapten derivative that has been provided with an available site for reaction, such as by the attachment of a linking group, for synthesizing a hapten derivative conjugate.

As used herein, a "linking group" or "linker" refers to a portion of a chemical structure which connects two or more substructures such as haptens, carriers, immunogens, labels, tracers or other linkers. A linking group has at least 1 uninterrupted chain of atoms other than hydrogen (or other monovalent atoms) extending between the substructures. The atoms of a linking group and the atoms of a chain within a linking group are themselves connected by chemical bonds. Linkers may be straight or branched, saturated or unsaturated, carbon chains. They may also include one or more heteroatoms within the chain or at termini of the chains. By "heteroatoms" is meant atoms other than carbon which are chosen from the group consisting of oxygen, nitrogen and sulfur. Linking groups may also include cyclic or aromatic groups as part of the chain or as a substitution on one of the atoms in the chain.

The number of atoms in a linking group or linker is determined by counting the atoms other than hydrogen. The number of atoms in a chain within a linking group is determined by counting the number of atoms other than hydrogen along the shortest route between the substructures being connected.

Linking groups may be used to activate, e.g., provide an available site on a hapten for synthesizing a conjugate of a hapten with a label or carrier.

The terms "immunogen" and "immunogenic" as used herein refer to substances capable of producing or generating an immune response in an organism.

An "active ester" refers to an ester group that can react with a free amino group of compounds such as, for example, peptides and proteins. Examples of active esters include N-hydroxysuccinimide, p-nitrophenyl, pentafluorophenyl, and N-benzotriazolyl.

A "carrier" or "immunogenic carrier," as the terms are used herein, is an immunogenic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, particles, and nucleic acids that are recognized as foreign and thereby elicit an immunologic response from the host.

Various protein types may be employed as a poly(amino acid) immunogenic carrier. These types include albumins, serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic poly(amino acids) may be utilized.

The immunogenic carrier can also be a polysaccharide, which is a high molecular weight polymer built up by repeated condensations of monosaccharides. Examples of polysaccharides are starches, glycogen, cellulose, carbohydrate gums such as gum arabic, agar, and so forth. The polysaccharide can also contain poly(amino acid) residues and/or lipid residues.

The immunogenic carrier can also be a poly(nucleic acid) either alone or conjugated to one of the above mentioned poly(amino acid)s or polysaccharides.

The immunogenic carrier can also be a particle. The particles are generally at least about 0.02 microns (μm) and not more than about 100 μm, and usually about 0.05 μm to 10 μm in diameter. The particle can be organic or inorganic, swellable or non-swellable, porous or non-porous, optionally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acid)s will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms "peptide", "polypeptide" and "poly(amino acid)" are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, and hapten radioactive isotopes.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, urine, tears, cells, organs, tissues, bone, bone marrow, lymph, lymph nodes, synovial tissue, chondrocytes, synovial macrophages, endothelial cells, and skin.

The term "patient" includes human and animal subjects.

The present invention provides efavirenz hapten derivatives that are useful for the preparation of immunogens and conjugates for use in immunoassays for the detection of efavirenz.

By attaching an efavirenz derivative according to the present invention to an immunogenic carrier material, antisera and polyclonal antibodies, as well as monoclonal antibodies, can be produced and isolated, which are useful reagents for immunoassays for the detection of efavirenz.

The derivatives can also be coupled to a variety of labels by methods well known in the art to provide a variety of reagents useful in various immunoassay formats. For detection, there can be attached detector molecules such as fluorophores, for example, fluorescein, or radiolabeled or chemiluminescent groups to produce tracers. The hapten can be bound to microparticles including colored latex for use in spectrophotometric or direct optical detection formats such as latex agglutination and chromatographic strip tests. The attached group may also be an indirect detection molecule such as an energy transfer partner, enzyme or other group which is detected by further chemical reaction.

Coupling can be accomplished by any chemical reaction that will bind the label or carrier. This linkage can include many chemical mechanisms, for instance covalent binding, affinity binding, intercalation, coordinate binding, and complexation. Most often, the linkage is made through covalent bonding. Covalent binding can be achieved either by direct condensation of existing side chains or by incorporation of external bridging molecules. Many bivalent or polyvalent linking agents are useful in coupling protein molecules, such as a carrier, to other molecules. Representative coupling agents include organic compounds such as thioesters, carbodiimides, N-hydroxysuccinimide esters, diisocyanates, glutaraldehyde, diazobenzenes, and hexamethylene diamines. This listing is not an exhaustive compilation of the various classes of coupling agents known in the art but, rather, is representative of the more common coupling agents. (See Killen et al., *J. Immunol.* 133:1335-2549, 1984; Jansen, F. K., et al., *Immunological Reviews* 62:185-216, 1982; and Hermanson, G., "Bioconjugate Techniques", Academic Press, 1995.

The present invention provides a compound having the structure:

where L is NH or O, $R_1$ is a saturated or unsaturated, substituted or unsubstituted, straight or branched chain of 0-10 carbon or hetero atoms, X is a linker group consisting of 0-2 substituted or unsubstituted aromatic rings or aliphatic linking groups containing 0-10 carbon or hetero atoms, and Y is an activated ester, maleimido group, thiol, or NH-Z where Z is a carrier or a label.

A central feature of the synthesis of an efavirenz immunogen according to the present invention is the preparation of an efavirenz analog by alkylation or acylation of a phenolic or amino group on the aromatic ring of efavirenz. The overall synthesis of the immunogen requires building up the benzoxazinone ring system. Synthesis of the efavirenz analog containing a phenolic group starts with the protection of the phenolic group of 5-hydroxy 2-nitro benzaldehyde (1) using an acid-sensitive protecting group, especially 2-methoxy ethoxy methyl (MEM) ether. Cesium fluoride catalyzed trifluoromethylation of aldehydes with trifluoromethyl trimethylsilane is known in the literature (*J. Org Chem.* 64, 2873, 1999). Trifluoromethylation of 5-OMEM-2-nitrobenzaldehyde (2) can be carried out in the presence of trifluoromethyl trimethylsilane in the presence of cesium fluoride at temperature ranging from 20° to 30° C.

Reduction of a nitro group to an amino group is known in the literature and can be carried out under various reaction conditions by a person skilled in the art to which the present invention belongs.

The reduction of the nitro group of the fluorinated product (3) is carried out under hydrogenation conditions, preferably with 10% Pd—C under 50 psi to give the desilylated amino alcohol product (4). Protection of an aromatic amino group as a t-Boc group is known in the literature (see "Protective Groups in Organic Synthesis", $2^{nd}$ edition, T. Greene and P. Wuts, Wiley-Interscience, 1991). The amino alcohol (4) is protected as a t-BOC group using di-t-butyldicarbonate in the presence of sodium carbonate to give 5.

Oxidation of a secondary alcohol to a ketone can be carried out under a variety of reaction conditions, e.g., PCC, PDC, $CrO_3$, preferably using oxalyl chloride/DMSO under Swern oxidation conditions. Thus in Example 4, compound 5 was reacted with oxalyl chloride in the presence of DMSO at a temperature of −40° to −60° C. in dichloromethane to give 6. Nucleophilic addition to a carbonyl group can be carried out under various reaction conditions including Grignard addition or addition with lithiated nucleophiles. The nucleophilic addition reaction of lithiated cyclopropyl acetylide on the trifluoromethyl ketone of efavirenz analog (6) results in the addition product (7). This addition product (7) can undergo cyclization into a benzoxazinone ring system by reaction with n-butyl lithium in the presence of a solvent, preferably toluene under refluxing conditions to give 8. This type of cyclization to prepare efavirenz is known in the literature (*Synthetic Communication* 27, 4373, 1997). Deprotection of the 2-methoxy ethoxy methyl ether can be done under acidic conditions, preferably using trifluoroacetic acid. Thus in Example 6, the MEM group of benzoxazinone derivative (8) was deprotected using trifluoroacetic acid to give 9. Alkylation reaction of a phenolic hydroxyl group can be carried out using an alkyl halide in the presence of a base, such as sodium hydride, sodium carbonate, potassium carbonate, cesium carbonate, preferably potassium carbonate with or without the presence of a phase transfer catalyst. Thus in Example 7, the alkylation reaction of the efavirenz analog (9) with an ethyl-4-bromobutyrate was carried out in the presence of potassium carbonate at a temperature ranging from 50° to 150° C. in acetone in the presence of a phase transfer catalyst 18-crown-6 to give 10. The deprotection of an alkyl ester group can be done under mild basic conditions or acidic conditions, preferably using lithium hydroxide under aqueous alcohol.

Thus in Example 9, 10 was reacted with lithium hydroxide in aqueous methanol to give the hydrolyzed carboxylic acid product 11. The acid derivative was converted to an active ester and then conjugated to a protein. The alkylation reaction on efavirenz analog (9) can also be done using a haloalkyl chain with a protected amine (see FIG. 3). The protection group for the amine can be a t-BOC (acid-labile protecting group) or a phthalimide or FMOC (base-labile protecting group). The alkyl group linker serves the purpose of providing an additional spacer between the properly functionalized efavirenz analog and the protein or peptide. Linker extension may be used at this stage to generate terminal activating groups such as active esters, isocyanates, thiols, and maleimides. For example, reaction of the amino group containing efavirenz derivative with one end of the homobifunctional N-hydroxysuccinimide esters of bis-carboxylic acids such as terephthalic acid will generate stable N-hydroxysuccinimide ester terminated linker adducts (18) which are useful for conjugation to amines on polypeptides, polysaccharides, and labels. Linker extension can also be accomplished with heterobifunctional reagents to give a maleimido functionality (19) for subsequent conjugation to thiol groups on polypeptides and labels (see FIGS. 4 and 5). Alternatively, an amino-terminated linker can be extended with a heterobifunctional thiolating reagent that reacts to form an amide bond at one end and a free or protected thiol at the other end. Some examples of thiolating reagents of this type, which are well known in the art, are 2-iminothiolane (2-IT), succinimidyl acetylthiopropionate (SATP), and succinimido 2-pyridyldithiopropionate (SPDP). The incipient thiol group is then available to form thiol ethers with maleimide modified immunogens or labels. Another approach to generate an acylated derivative with urea or thiourea bonds at the point of attachment to the amino linked efavirenz derivative is to react the amino functionality of the efavirenz derivative with 4-nitrochloroformate, phosgene, or thiophosgene. The later intermediates react readily with amines (from aminodextran, protein, or peptides) to give a urea or thiourea. Alternative phosgene equivalents such as carbonyldiimidazole (see FIG. 6) or disuccinimidyl carbonate will react similarly.

Besides the 6-position hydroxy derivative (9), a 6-position amino-functionalized efavirenz derivative (23) can be prepared according to the literature procedure (*Bioorganic & Medicinal Chemistry Letters* 9, 3221, 1991).

Extension on the amino group of the efavirenz analog (23) can be done by acylation reaction of the amino group, preferably with succinic anhydride in the presence of a base as described in FIG. 7. The acid derivative can be functionalized as an active ester, preferably as an N-hydroxysuccinimide ester (25) which is suitable for attachment to polypeptides and proteins to give compound 26.

Active esters of the present invention, e.g., compounds 12, 18, and 25, are reactive with nucleophiles, especially primary amines, at relatively low temperature in aqueous and nonaqueous solvent mixtures. The immunogenic carrier is typically a polypeptide or a polysaccharide with a molecular weight of more than 100 kD. Examples of preferred carriers are keyhole limpet hemocyanin (KLH) and bovine thyroglobulin (BTG). Reaction between the activated hapten and the amino group on the carrier is typically carried out in a buffered mixture of water and a water-miscible organic solvent such as DMSO at room temperature at a pH from about 6 to about 8.

The following examples serve merely to illustrate certain aspects of the invention and should not be viewed as limiting the invention in scope or spirit.

Specific Embodiments

EXAMPLE 1

Synthesis of
5-(2-methoxy-ethoxymethoxy)-2-nitro-benzaldehyde
(2)

A suspension of 5 g (30 mmol) of 5-hydroxy-2-nitrobenzaldehyde (1) in 100 mL of dichloromethane and 10 mL of freshly distilled tetrahydrofuran was cooled to 0° C. To this suspension 6.25 mL (57 mmol) of N,N-diisopropylethylamine was added, and the resulting reaction mixture was stirred for 5 minutes. To this reaction mixture 3.76 mL (33 mmol) of 2-methoxyethoxymethyl chloride was added, stirred for 10 minutes at 0° C., warmed up to room temperature, and allowed to stir at room temperature for 18 hours. The reaction mixture was concentrated under reduced pressure, and 150 mL of ethyl acetate were added. The resulting off-white precipitate was filtered off, and the filtrate was transferred into a separatory funnel. The organic layer was washed with 75 mL of 1N sodium hydroxide solution, 100 mL water, and 75 mL brine. The organic layer was dried over anhydrous potassium carbonate, filtered, and concentrated to give 7.4 g (29 mmol, 97%) of 2 [LC-MS; M+Na 278].

EXAMPLE 2

Synthesis of Trimethyl-{2,2,2-trifluoro-1-[5-(2-methoxy-ethoxymethoxy)-2-nitro-phenyl]-ethoxy}-silane (3)

To a solution of 2 g (7.8 mmol) of 2 was added 5 mL of acetonitrile followed by 2 mL (13.5 mmol) of trimethyl (trifluoromethyl) silane and 20 mg (0.13 mmol) of cesium fluoride. The reaction mixture was allowed to stir at room temperature under argon for 10 minutes. The reaction mixture turned brown during this period. It was concentrated and purified by silica gel flash column chromatography using dichloromethane as an eluent to give 2.89 g (7.3 mmol, 93%) of 3.

EXAMPLE 3

Synthesis of [4-(2-methoxy-ethoxymethoxy)-2,2,2-trifluoro-1-hydroxy-ethyl)-phenyl]-carbamic Acid Tert-Butyl Ester (5)

A solution of 3.9 g (9.8 mmol) of 3 in 75 mL of methanol was prepared, and argon was bubbled through it for about 2 minutes. To this solution 280 mg of 10% Pd—C and 4 drops of glacial acetic acid were added, and the resulting mixture was hydrogenated under 50 psi in a Pars apparatus for 2 hours. The resulting mixture was filtered through CELITE (Celite Corp.), and the filtrate was concentrated under reduced pressure. The product 1-[2-amino-5-(2-methoxy-ethoxymethoxy)-phenyl]-2,2,2-trifluoro-ethanol (4) was used in Example 4 without further purification.

To all of 4 was added 50 mL of water, 50 mL of THF, 2.5 g (23.5 mmol) of sodium carbonate, and 2.5 g (11.4 mmol) of di-t-butyl dicarbonate. The resulting reaction mixture was allowed to stir at room temperature for 72 hours, and the volatile solvent was removed under reduced pressure. To the resulting residue 20 mL of water was added, and the aqueous mixture was extracted with 5×40 mL of dichloromethane. The organic layers were combined, dried ($Na_2SO_4$), and concentrated. The residue was purified by silica gel flash column chromatography using 2:1, hexane:ethyl acetate as eluent to give 1.18 g (2.98 mmol, 30% in two steps) of product (5) as a light brown gum [LC-MS; M+Na 418.1].

EXAMPLE 4

Synthesis of [4-(2-methoxy-ethoxymethoxy)-2-(2,2,2-trifluoro-acetyl)-phenyl]-carbamic Acid Tert-Butyl Ester (6)

A solution of 410 μL (4.6 mmol) of oxalyl chloride in 20 mL of dichloromethane was cooled to −40° to −60° C., and 650 μL (9.1 mmol) of anhydrous DMSO were added slowly to the reaction. The solution was allowed to stir at −40° C. to −60° C. for 55 minutes, and a solution of 450 mg (1.1 mmol) of 5 in 1 mL of dichloromethane was added. The reaction mixture was allowed to stir at −40° to −60° C. for 55 minutes, and 1 mL (7.1 mmol) of triethylamine was added followed by 20 mL of water. The resulting reaction mixture was allowed to stir for 2 hours, and the organic part was separated, washed with 20 mL of water, dried (anhydrous $Na_2SO_4$), and concentrated under reduced pressure. The residue was purified by flash silica gel column chromatography using dichloromethane to give 400 mg (1.0 mmol, 89%) of 6 as a bright yellow oil [LC-MS; M+K 432].

EXAMPLE 5

Synthesis of [2-(3-cyclopropyl-1-hydroxy-1-trifluoromethyl-prop-2-ynyl)-4-(2-methoxy-ethoxymethoxy)-phenyl]-carbamic Acid Tert-Butyl Ester (7)

A solution of 200 μL (2.3 mmol) of ethynyl-cyclopropane in 2 mL of freshly distilled THF was cooled to −40° C. and 1 mL (2.5 mmol) of n-butyl lithium (2.5M in hexane) was added under argon atmosphere. The reaction mixture was allowed to stir at −40° C. for 10 minutes. To the reaction mixture a solution of 400 mg (1.0 mmol) of 6 in 4 mL of freshly distilled THF was added, and the reaction was allowed to stir at −40° C. for 15 minutes. To the reaction mixture 2 mL of isopropanol were added followed by 20 mL of saturated ammonium chloride solution at −40° C. The reaction mixture was warmed up to room temperature, and 30 mL of dichloromethane was added. The organic layer was separated, and the aqueous layer was extracted with 3×30 mL of dichloromethane. The organic layers were combined, dried (anhydrous $Na_2SO_4$), and concentrated under reduced pressure. The residue was purified by silica gel flash column chromatography using 20% ethyl acetate in hexane to give 280 mg (0.61 mmol, 60%) of 7 [LC-MS; M+Na 482.2].

EXAMPLE 6

Synthesis of 4-cyclopropylethynyl-6-(2-methoxy-ethoxymethoxy)-4-trifluoromethyl-1,4-dihydro-benzo[d][1,3]oxazin-2-one (8)

To 1.2 g (2.6 mmol) of 7 was added 15 mL of toluene, and the reaction mixture was cooled to 0° to −4° C. under argon atmosphere. To the reaction mixture 1.4 mL (3.5 mmol) of n-butyl lithium (2.5M in hexane) was added, and the resulting reaction mixture was allowed to stir at 0° to −4° C. for 10 minutes, warmed up to room temperature, and allowed to reflux for 1 hour. The reaction mixture was concentrated. Then 20 mL of water was added and the aqueous layer was extracted with 4×20 mL of dichloromethane. Organic layers were combined, dried ($Na_2SO_4$), and concentrated. The residue was purified by silica gel flash column chromatography using 20% ethyl acetate in hexane to give 965 mg (2.5 mmol, 96%) of 8 as a light brown oil [LC-MS; M+H 386.1].

Synthesis of 4-cyclopropylethynyl-6-hydroxy-4-trifluoromethyl-1,4-dihydro-benzo[d][1,3]oxazin-2-one (9)

To 150 mg (0.39 mmol) of 8 was added 2 mL of trifluoroacetic acid. The mixture was allowed to stir at room temperature for 2 hours. The reaction mixture was concentrated under reduced pressure, and the residue was purified by preparative thin layer chromatography (2 mm silica gel plate, E. Merck) using 5% methanol in dichloromethane to give 110 mg (0.37 mmol, 96%) of 9 as a colorless oil [LC-MS; M+H 298.1].

EXAMPLE 7

Synthesis of 4-(4-cyclopropylethynyl-2-oxo-4-trifluoromethyl-1,4-dihydro-2H-benzo[d][1,3]oxazin-6-yloxy)-butyric Acid Ethyl Ester (10)

To 120 mg (0.40 mmol) of 9 were added 12 mL of anhydrous acetone, 120 mg (0.86 mmol) of anhydrous potassium carbonate, 2 mg of 18-crown-6 and 40 µL (0.28 mmol) of ethyl 4-bromobutyrate. The reaction mixture was allowed to stir at 56° C. for 3 hours and was concentrated under reduced pressure. To the residue 20 mL of water were added followed by 1 mL of 1N HCl. The aqueous layer was extracted with 4×20 mL of dichloromethane. The organic layers were combined, dried ($Na_2SO_4$), and concentrated under reduced pressure. The residue was purified by preparative thin layer chromatography (silica gel, 2 mm thickness, E. Merck) using 1% methanol in dichloromethane to give 45 mg (0.11 mmol, 27%) of 10 as a colorless thick oil [LC-MS; M+H 412.1].

EXAMPLE 8

Synthesis of 4-(4-cyclopropylethynyl-2-oxo-4-trifluoromethyl-1,4-dihydro-2H-benzo[d][1,3]oxazin-6-yloxy)-butyric Acid (11)

To a suspension of 45 mg (0.11 mmol) of 10 in 4 mL of 50% methanol in water was added 60 mg (2.5 mmol) of lithium hydroxide. The reaction mixture was allowed to stir at room temperature for 1 hour and concentrated under reduced pressure. To the residue 20 mL of water were added followed by 1 mL of 1N HCl. The reaction mixture was extracted with 4×30 mL of ethyl acetate. The organic layers were combined, dried ($Na_2SO_4$), and concentrated under reduced pressure. The residue was purified by preparative thin layer chromatography (silica gel, 2 mm thickness, E. Merck) using 5% methanol in dichloromethane to give 35 mg (0.091 mmol, 83%) of 11.

EXAMPLE 9

Synthesis of 4-(4-cyclopropylethynyl-2-oxo-4-trifluoromethyl-1,4-dihydro-2H-benzo[d][1,3]oxazin-6-yloxy)-butyric Acid 2,5-dioxo-pyrrolidin-1-yl Ester (12)

A solution of 35 mg (0.091 mmol) of the acid 11 in 2 mL of anhydrous THF was cooled to 0° C., and 30 µL (0.15 mmol) of N,N-diisopropylethylamine was added followed by 40 mg (1.28 mmol) of O-(N-succinimidyl)-N,N,N',N'-tetramethyluronium tetrafluoroborate. The reaction mixture was allowed to warm up to room temperature. The reaction mixture was concentrated under reduced pressure, and the residue was purified by RP preparative HPLC using acetonitrile and water as a mobile phase containing 0.1% of trifluoroacetic acid to give 30 mg (00.62 mmol, 68%) of 12 as a white powder [LC-MS; M+H 481.0].

EXAMPLE 10

KLH Conjugate Using Efavirenz Analog Activated Ester (13)

A solution of 68 mg of keyhole limpet hemocyanin (KLH) in 4.5 ml of 50 mM potassium phosphate (pH 7.5) was cooled in an ice bath. 5 mL of DMSO were added to the solution dropwise, and the reaction temperature was maintained below room temperature. Then a solution of 25 mg (0.052 mmol) of 12 in 0.5 mL of DMF was added to the protein solution dropwise. The mixture was allowed to stir at room temperature 18 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (1 L each for at least 6 hours each). The protein concentration was determined to be 2.1 mg/mL using BioRad Coomassie blue protein assay (Bradford, M., *Anal. Biochem.* 72, 248, 1976). A total of 20 mL of the conjugate was obtained. The extent of available lysine modification was determined to be 60% by the TNBS method (Habeeb AFSA, *Anal. Biochem.* 14, 328-34,1988).

EXAMPLE 11

BSA Conjugate Using Efavirenz Analog Activated Ester (14)

A solution of 475 mg of bovine serum albumin (BSA) in 5 mL of 50 mM potassium phosphate (pH 7.5) was cooled in an ice bath. To the solution was added 7 mL of DMSO dropwise, and the reaction mixture was maintained below room temperature. To the protein solution was added a solution of 10 mg (0.020 mmol) of 12 in 1 mL of anhydrous DMF dropwise. The reaction mixture was allowed to stir at room temperature 48 hours. The resulting conjugate was placed in a dialysis tube (10,000 MW cut-off) and was dialyzed in 1 L of 70% DMSO in 50 mM potassium phosphate (pH 7.5, 3 changes, at least 3 hours each), 1 L of 50% DMSO in 50 mM potassium phosphate (at least 3 hours), 1 L of 30% DMSO in 50 mM potassium phosphate (at least 3 hours), 1 L of 10% DMSO in 50 mM potassium phosphate (at least 3 hours) at room temperature, followed by 6 changes with 50 mM potassium phosphate (pH 7.5) at 4° C. (1 L each) The protein concentration was determined to be 7.12 mg/mL using BioRad Coomassie blue protein assay. A total of 45 mL of the conjugate was obtained.

EXAMPLE 12

Synthesis of N-(4-cyclopropylethynyl-2-oxo-4-trifluoromethyl-1,4-dihydro-2H-benzo[d][1,3]oxazin-6-yl)-succinamic Acid (24)

To a solution of 100 mg (0.33 mmol) of 23 in 25 mL of 1,2 dichloroethane is added 50 mg (0.5 mmol) of succinic anhydride, 0.50 mL (0.35 mmol) of triethylamine and 20 mg (0.16 mmol) of 4-(dimethylamino)pyridine. The reaction mixture is heated to reflux for 1.5 hours and cooled to room temperature. The organic layer is washed with a 5% aqueous solution of ammonium chloride, water, dried ($Na_2SO_4$), and concentrated to give the acid 24.

EXAMPLE 13

Synthesis of N-(4-cyclopropylethynyl-2-oxo-4-trifluoromethyl-1,4-dihydro-2H-benzo[d][1,3]oxazin-6-yl)-succinamic Acid 2,5-dioxo-pyrrolidin-1-yl Ester (25)

The activated ester 25 is prepared from 24 following the procedure described in Example 10 for the conversion of 11 to 12.

EXAMPLE 14

Synthesis of 6-amino-4-cyclopropylethynyl-4-trifluoromethyl-1,4-dihydro-benzo[d][1,3]oxazin-2-one (23)

The amino benzoxazinone derivative 23 can be prepared according to the procedure described in *Bioorganic & Medicinal Chemistry Letters* 9, 3221-3224, 1999.

EXAMPLE 15

Development of Monoclonal Antibodies to Efavirenz

Female Balb/c mice 16 weeks of age were immunized with efavirenz-KLH immunogen (13). Initial immunizations were of 100 μg of immunogen emulsified in Freund's Complete Adjuvant, given via intraperitoneal route. Approximately three week intervals were allowed to pass between immunizations. All following immunizations were of the same dosage emulsified in Freund's Incomplete Adjuvant also via intraperitoneal injection. A total of four immunizations were given.

Fusion

Four days subsequent to the last immunization, the mouse was killed by cervical dislocation and the spleen harvested. The spleen was processed by grinding between two sterile frosted glass slides in warmed cell culture media. The liberated cells were taken up into a sterile 15 ml centrifuge tube and large fragment allowed to settle for 1-2 minutes. The suspended cells were pipetted into a separate sterile 50 ml centrifuge tube and sample taken for counting. Myeloma cells, of the F0 strain (ATCC) were added at a ratio of 1 to 5 splenocytes and the resulting mixture centrifuged to settle the cells into a compact pellet. Fusion comprised adding myeloma cells (⅕ the number of lymphocytes), washing via centrifugation, resuspension in serum-free warm Iscove's Modified Dulbecco's Media (IMDM, Irvine Scientific), and re-centrifugation. The centrifuge tubes containing the resulting pellets were gently tapped to loosen the cells, then 1 ml of warmed PEG/DMSO solution (Sigma Chemicals) was slowly added with gentle mixing. The cells were kept warm for 1.5 minutes, after which pre-warmed, serum-free IMDM was added at the following rates: 1 ml/min, 2 ml/min, 4 ml/min, and 10 ml/min, then the tube was filled to 50 ml, sealed, and incubated for 15 minutes. The cell suspensions were centrifuged, the supernatant decanted, and IMDM containing 10% fetal calf serum (Summit Biologicals) was added. The cells were centrifuged once again and resuspended in complete cloning medium. This was comprised of IMDM, 10% FCS, 10% Condimed H1 (Roche Molecular Systems), 4 mM glutamine, 50 μM 2-mercaptoethanol, 40 μM ethanolamine, and pen/strep antibiotics (all from Sigma). The cells were suspended at a density of $4 \times 10^5$ lymphocytes/ml, distributed 100 μl/well into sterile 96-well sterile microculture plates and incubated at 37° C. in 5% $CO_2$ for 24 hours. The next day, 100 μl of HMT selective medium (cloning medium+1:25 HMT supplement from Sigma Chemicals) was added. On the $6^{th}$ day of incubation, approximately 150 μl of media was drawn from each well using a sterile 8-place manifold connected to a light vacuum source. One hundred fifty microliters of HT media was then added. This was comprised of cloning medium+1:50 HT supplement (Sigma Chemicals). The plates were returned to the incubator and inspected daily for signs of growth. When growth was judged sufficient, wells were screened for antibody production via ELISA.

ELISA Screening

Microplates were coated with 100 μl efavirenz-BSA conjugate (14) in 0.1 M carbonate buffer, pH 9.5, for 1 hour at 37° C. (humidified). The plates were then emptied and filled with a post-coat solution consisting of Tris buffer, 1% gelatin hydrolysate, 2% sucrose, and 0.17% TWEEN 20 (all reagents were from Sigma Chemicals). The plates were incubated for an additional 1 hour at 37° C. (humidified) after which they were washed with phosphate-buffered saline containing 0.1% TWEEN 20. The plates were then filled briefly with a 2% sucrose solution in 0.15M Tris, pH 7.2-7.4, then emptied and allowed to air dry at room temperature. When dried, the plates were packed in zip-lock bags containing several desiccant pillows, sealed, and stored at 4° C. until use.

When the growing clones were judged ready for testing, 25 μl of supernatant from the wells were taken and transferred to 96-well flexible plates. Culture medium was added to each well to provide a 1:10 dilution of the media sample. Twenty five microliters of PBS-TWEEN were added to each well of one coated microplate, and 25 microliters of an 800 ng/ml solution of chiral efavirenz in PBS-TWEEN were added to the wells of another coated plate. Twenty five microliters of the diluted media samples were transferred to each of the coated plates above. The plates were incubated covered for 1 hour at 37° C., then washed with PBS-TWEEN. The wells were then filled with 100 μl of goat anti-mouse IgG-HRP conjugate (Zymed Labs) diluted in PBS-TWEEN and the plates re-incubated for 1 hour. The plates were then washed again, and 100 μl of K-Blue substrate (Neogen Corp) was added to each well. Color was allowed to develop for 5-15 minutes, then the reaction was stopped by the addition of 100 μl of 1 N HCl. Color was read via a microplate reader at 450 nm and collected by computer for analysis. The criteria for selection was binding to the efavirenz-BSA conjugate coated wells which received the PBS-TWEEN and reduced binding to the coated wells containing the free efavirenz drug.

The table below shows selected data from screening of the fusion plates and a subclone from a limiting dilution culture.

| Clone | Efavirenz-BSA | Efavirenz-BSA + Efavirenz |
|---|---|---|
| EFA-1 | 1.712 | 0.223 |
| EFA-2 | 1.196 | 0.225 |
| EFA-3 | 1.797 | 0.247 |
| EFA-4 | 1.448 | 0.069 |
| EFA-97 | 2.703 | 0.272 |
| EFA-97.1 | 3.059 | 0.381 |

Clones chosen were immediately subcloned via limiting dilution, and when ready, retested by the same method. Stable subclones were expanded, frozen in liquid nitrogen, and the spent media used to determine specificity using the cross-reactivity assay below.

Cross-reactivity Assay

Figure 1:
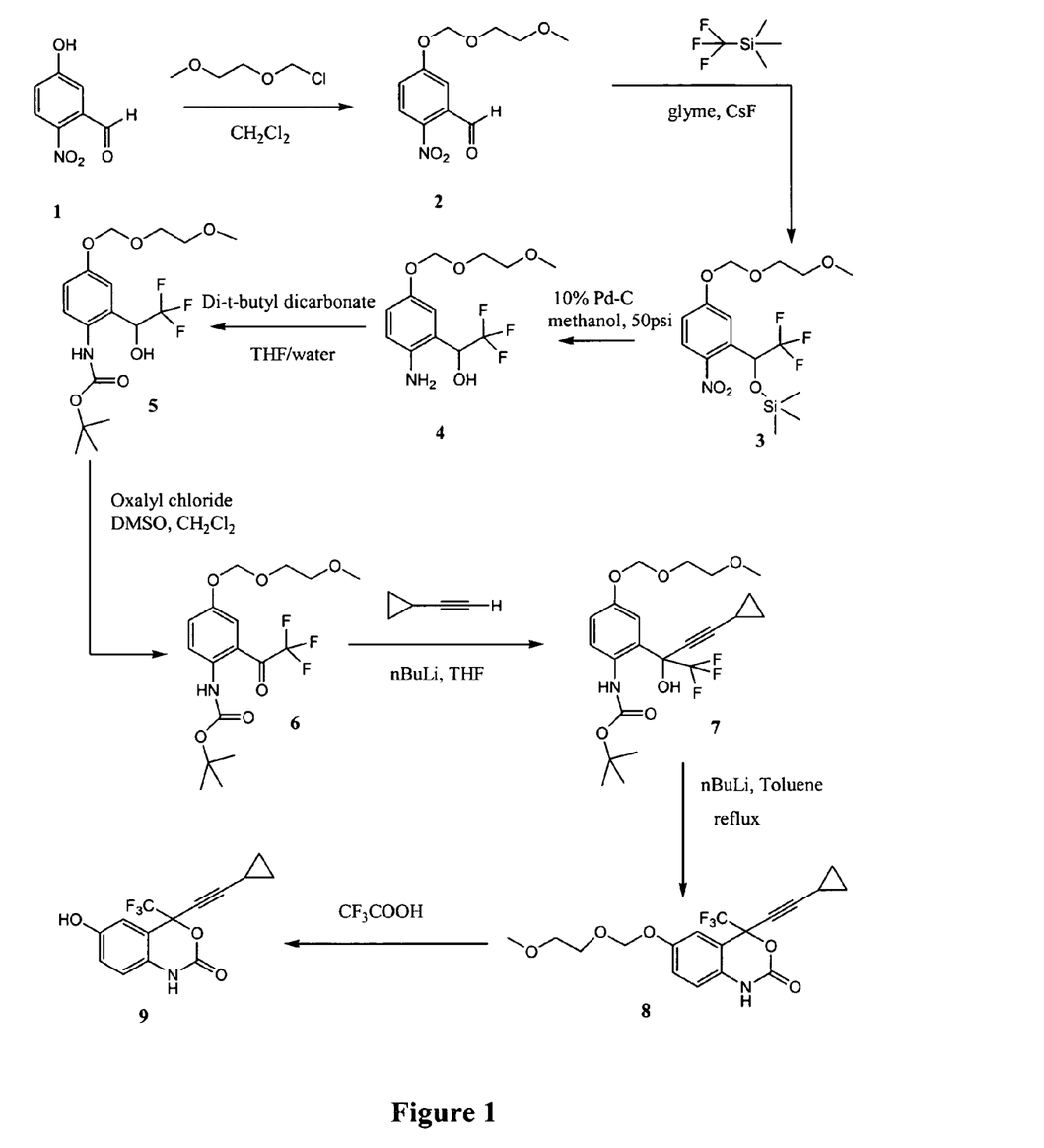
FIG. 1 is a schematic representation of a synthesis method for the 6-hydroxy analog of efavirenz, structure 9.
Figure 2:
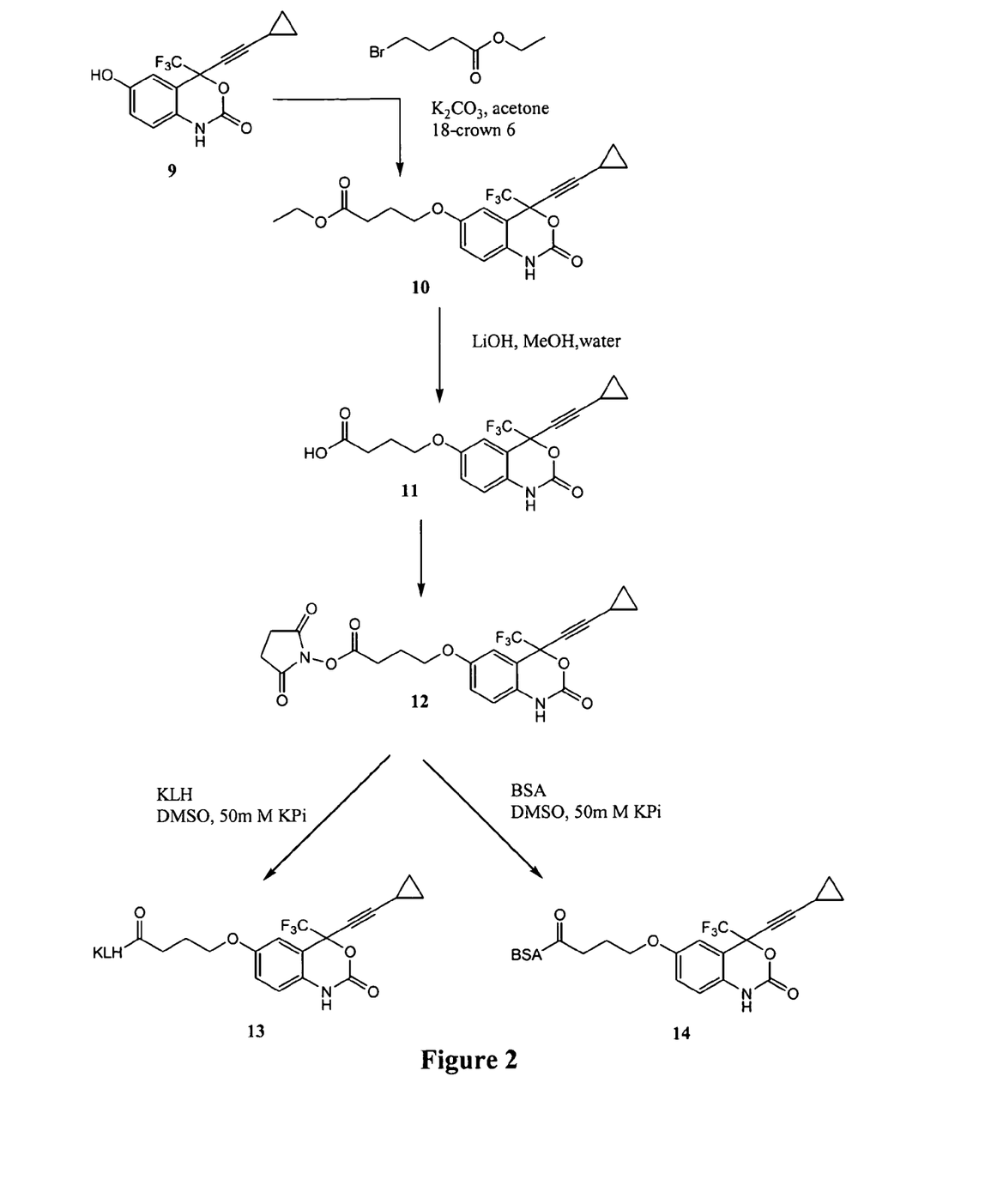
FIG. 2 is a schematic representation of a synthesis method for the KLH and BSA conjugates of efavirenz, structures 13 and 14.
Figure 3:
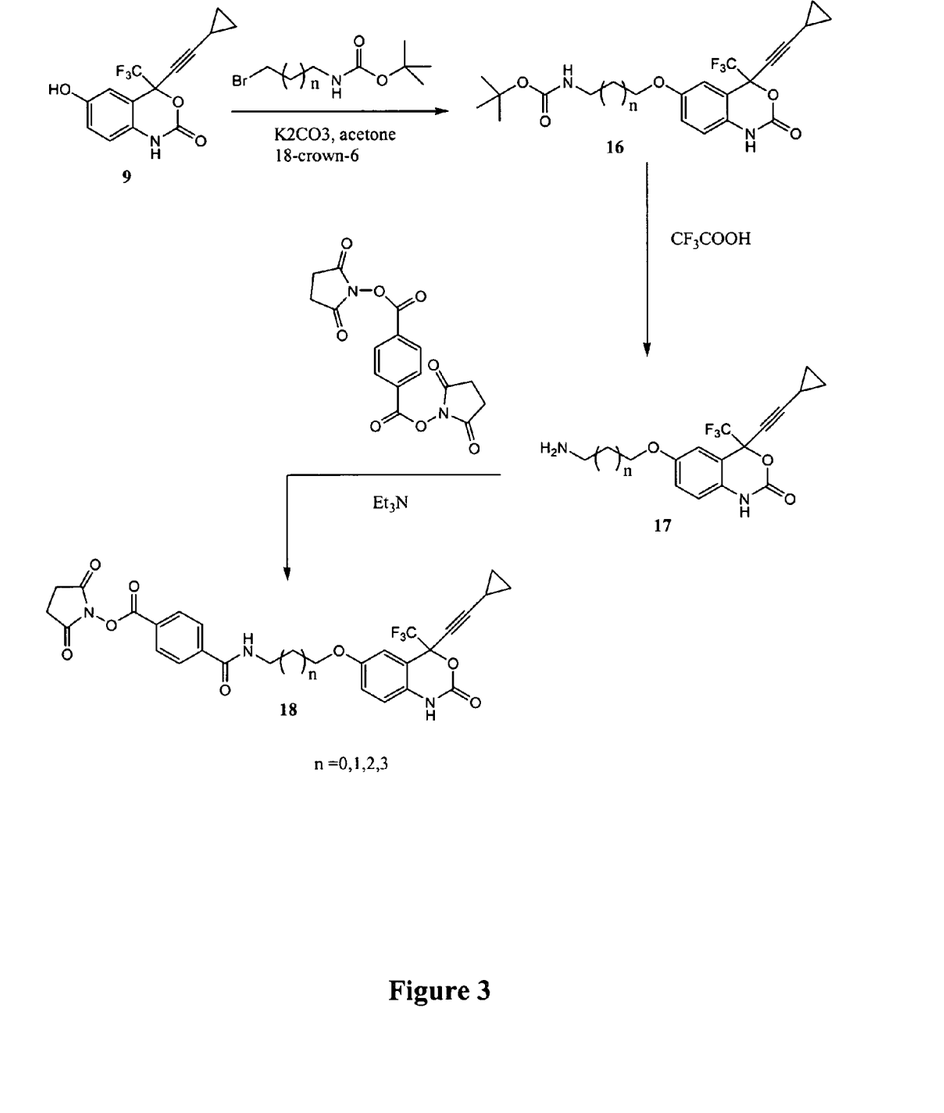
FIG. 3 is a schematic representation of a synthesis method for an activated ester of efavirenz with an aromatic linker.
Figure 4:
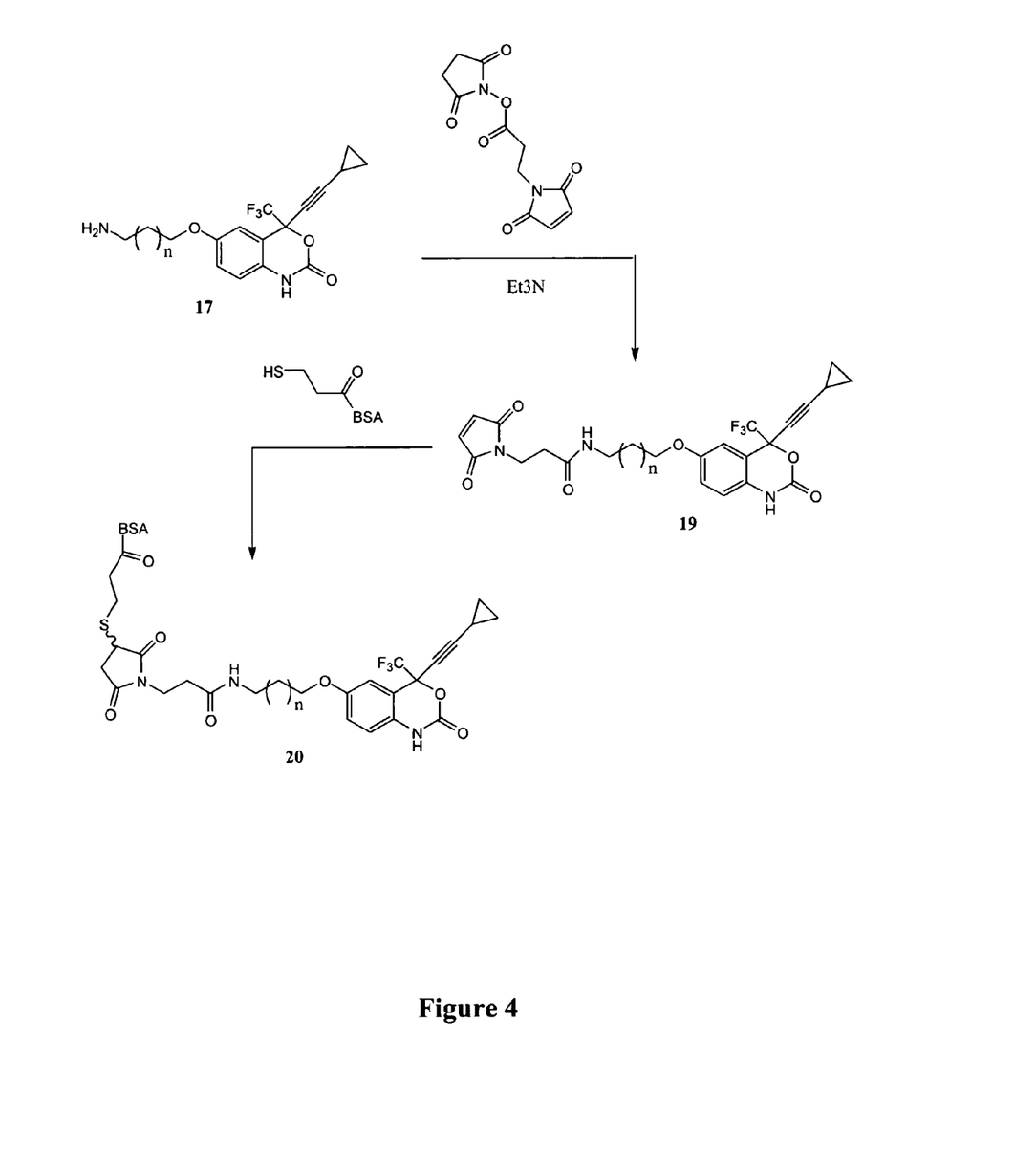
FIG. 4 is a schematic representation of a synthesis method for a protein conjugate using a maleimido efavirenz derivative.
Figure 5:
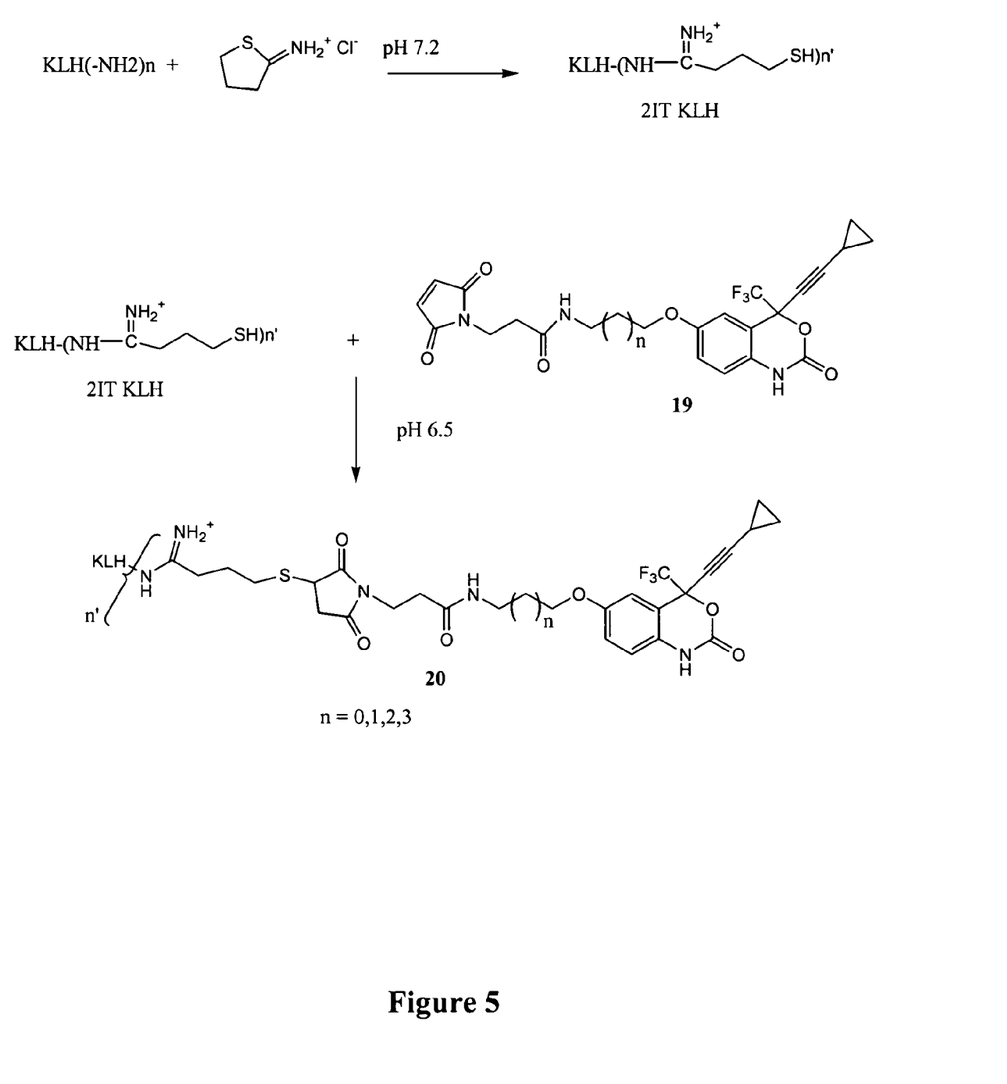
FIG. 5 is a schematic representation of a synthesis method for 2-iminothiolane KLH conjugate of efavirenz.
Figure 6:
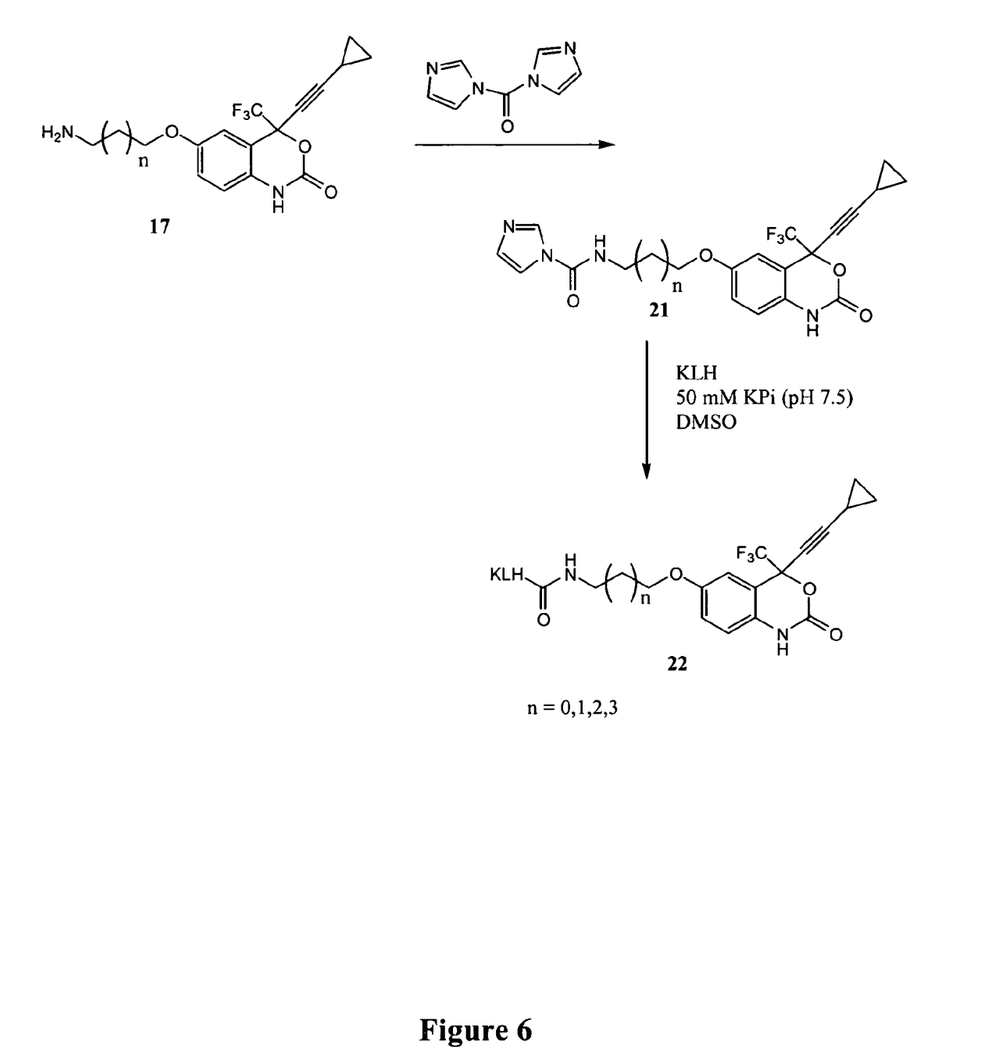
FIG. 6 is a schematic representation of a synthesis method for KLH conjugate using a carbonyl diimidazole derivative of efavirenz.
Figure 7:
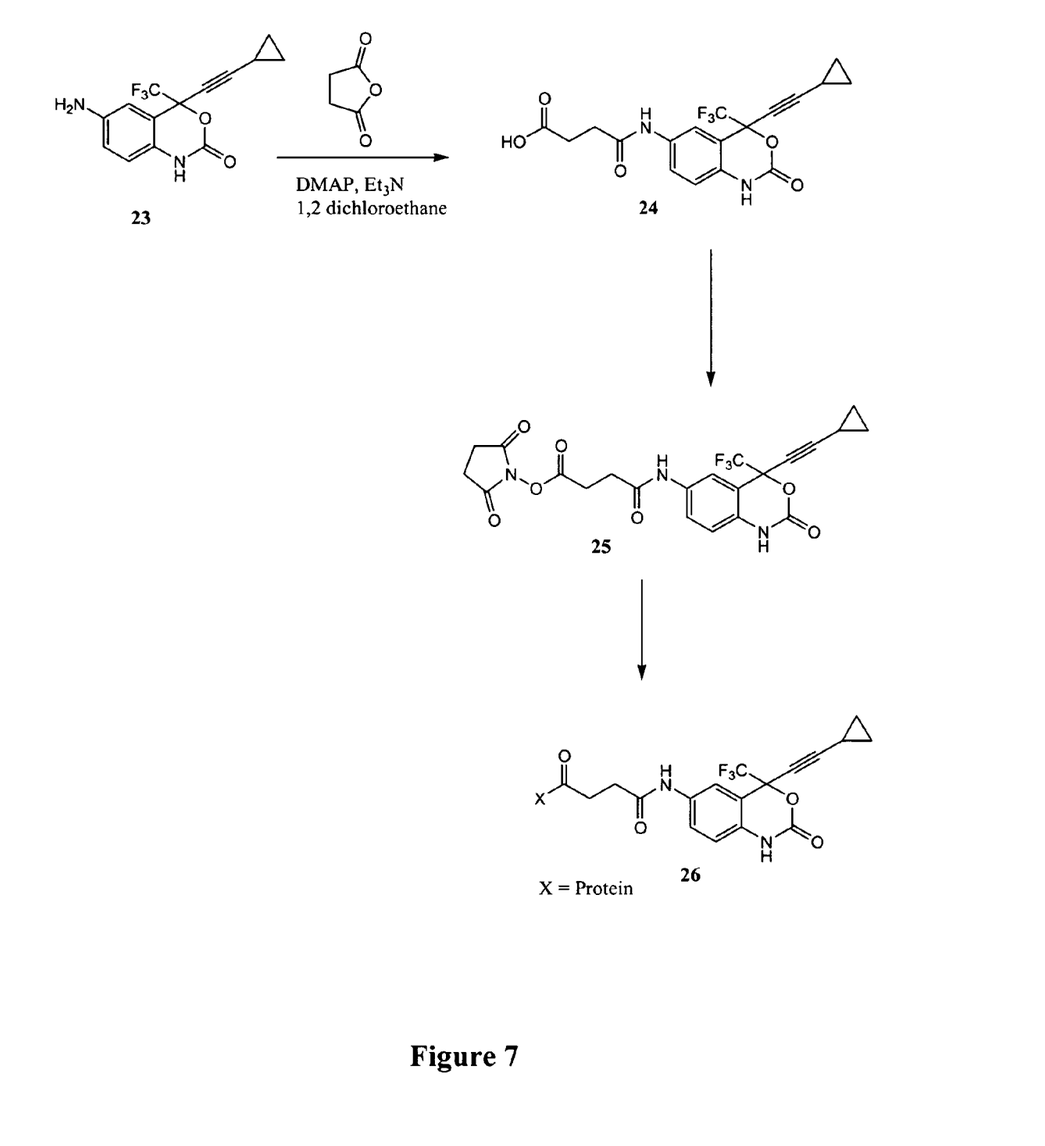
FIG. 7 is a schematic representation of a synthesis method for an alternative protein conjugate using 6-amino efavirenz.
Figure 8:
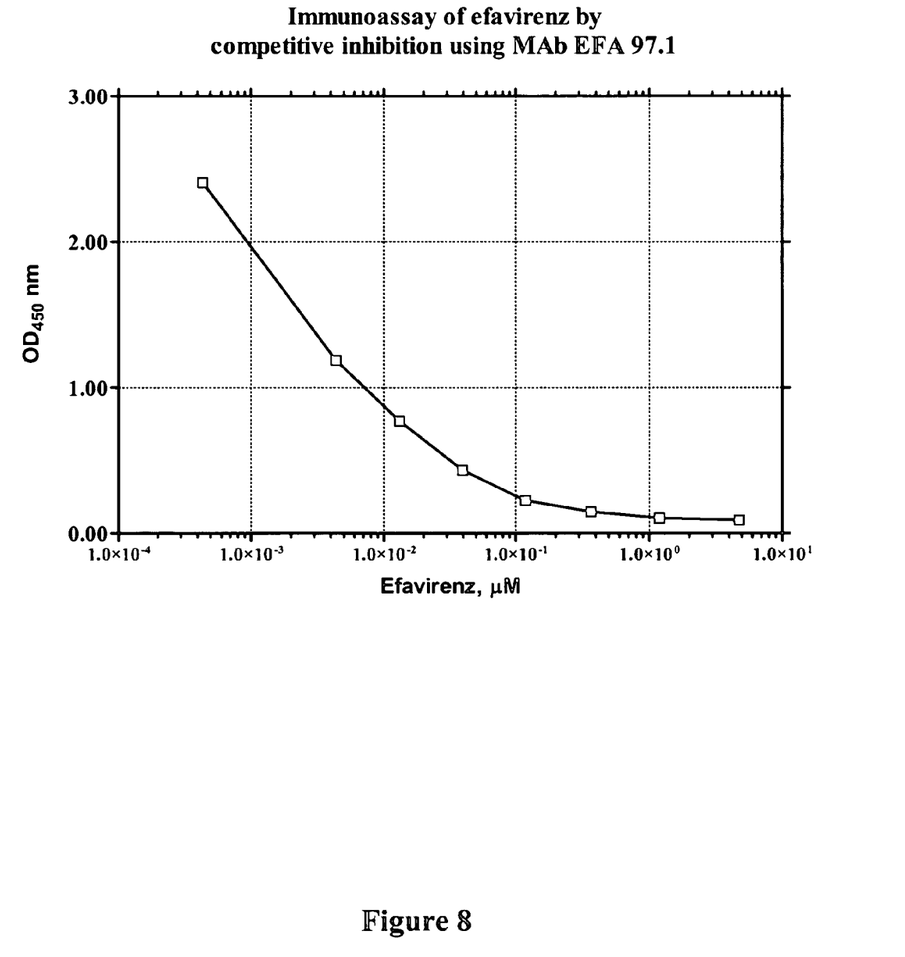
FIG. 8 is a graph showing response by free efavirenz in a competitive inhibition immunoassay using monoclonal antibody EFA 97.1.

Supernatants were subjected to serial dilutions and retested in the ELISA screen above omitting the competitive inhibition with free drug. The dilution providing for approximately a 50% reduction from the maximum OD was chosen for proceeding to cross-reactivity testing. This comprised repeating the preceding assay with the antibody at the chosen dilution and in the presence of varying concentrations of different drugs. FIG. 8 presents the results of such a determination. By determining the drug concentration resulting in a 50% reduction of binding ($ED_{50}$) of the standard drug, efavirenz, and dividing by the $ED_{50}$ of each other drug, and multiplying by 100, the following table of percent cross-reactivities of monoclonal antibody EFA 97.1 was calculated.

| Drug | % Cross-reactivity |
|---|---|
| efavirenz (chiral) | 100 |
| 3'-azido-3'-deoxythymidine | 0 |
| 2',3'-didehydro-3'-deoxythymidine | 0 |
| nevirapine | 0 |
| delaviridine | 0 |
| nelfinavir | 0 |
| saquinavir | 0 |
| indinavir | 0 |
| ritonavir | 0 |
| amprenavir | 0 |
| lopinavir | 0 |
| atazanavir | 0 |

This antibody, obtained via immunizations with efavirenz-KLH (racemic), surprisingly demonstrated a definite specificity toward the chiral, clinically relevant form of the drug. The antibody also demonstrated less than 1% cross-reactivity with other commonly co-administered drugs, including the NNRTI's nevirapine and delaviradine, the NRTI's 3'-azido-3'-deoxythymidine and 2',3'-didehydro-3'-deoxythymidine, and the PI's nelfinavir, saquinavir, indinavir, ritonavir, amprenavir, lopinavir, and atazanavir.

The murine hybridoma cell line EFA 97.1 was deposited with the American Type Culture Collection (ATCC, Manassas, Va.) on Feb. 17, 2004 and assigned ATCC designation PTA-5820.

Drug Quantitation by Immunoassay

Monoclonal antibody EFA-97.1 was used to develop an immunoassay to quantitate chiral efavirenz via competitive inhibition. Microplate wells were coated with test conjugate (14) at a concentration of 0.1 μg/ml under the same conditions as given for the ELISA screening above. The standard curve was carried out by preparing a dilution series of chiral efavirenz in PBS-T buffer, starting at 9.5 μM (micromole), and 1:3 dilutions into the same buffer. To wells in the coated microplate, 25 μl aliquots of the dilution series were added. This was followed by addition of 25 μl of antibody previously diluted to twice the concentration as used for the specificity determinations. The plate was sealed and incubated for 1 hour at 37° C. Following the incubation, the plate wells were washed 4 times with 200 μl of PBS-T buffer, and 50 μl of goat anti-mouse IgG-HRP antibody prediluted 1:5000 was added. The plate was sealed and returned to the incubator for 1 hour, after which the wells were washed with PBS-T buffer. The remainder of the assay was as given previously.

The dose response of optical density at 450 nm versus the drug concentration resulted in a curve by which the response of unknown samples could be compared and the efavirenz concentration thereby determined. FIG. 8 shows that the concentration range of the assay is from 0.0004 to 0.1 μM. Given the peak levels of 12.9 μM for this drug (Physician's Desk Reference), this indicates that a serum sample size of approximately 0.2 μl should be sufficient to cover the peak clinical concentration range of this drug. FIG. 8 is a graph showing response by free efavirenz in a competitive inhibition immunoassay.

What is claimed is:

1. A compound having the structure wherein L is NH or O;
$R_1$ is a saturated or unsaturated, substituted or unsubstituted, straight or branched chain of 0-10 carbon or hetero atoms;
X is a linker group consisting of 0-2 substituted or unsubstituted aromatic rings or aliphatic linking groups containing 0-10 carbon or hetero atoms; and
Y is an activated ester, maleimido group, thiol, or NH-Z where Z is a carrier or a label.

2. The compound of claim 1 wherein the carrier is selected front the group consisting of poly(amino acid)s, polysaccharides, poly(nucleic acid)s, and particles.

3. The compound of claim 1 wherein the label is selected from the group consisting of enzymes, enzyme fragments, radioactive isotopes, enzyme substrates, enzyme inhibitors, coenzymes, fluorogenic compounds, chemiluminescent materials, electrochemical mediators, reporter groups, nucleic acids and particles.

4. The compound of claim 1 wherein Y is an activated ester selected from the group consisting of N-hydroxysuccinimidyl, p-nitrophenyl, pentafluorophenyl, and N-hydroxybenzotriazolyl esters.

* * * * *